(12) United States Patent
Fan et al.

(10) Patent No.: US 10,923,214 B2
(45) Date of Patent: Feb. 16, 2021

(54) NEURAL NETWORK FOR PREDICTING DRUG PROPERTY

(71) Applicant: ACCUTAR BIOTECHNOLOGY INC., Brooklyn, NY (US)

(72) Inventors: Jie Fan, New York, NY (US); Ke Liu, Shanghai (CN); Xiangyan Sun, Shanghai (CN)

(73) Assignee: Accutar Biotechnology Inc., Brooklyn, NY (US)

( * ) Notice: Subject to any disclaimer, the term of this patent is extended or adjusted under 35 U.S.C. 154(b) by 244 days.

(21) Appl. No.: 16/125,533

(22) Filed: Sep. 7, 2018

(65) Prior Publication Data

US 2019/0108320 A1 Apr. 11, 2019

Related U.S. Application Data

(60) Provisional application No. 62/555,613, filed on Sep. 7, 2017.

(51) Int. Cl.
| | | |
|---|---|---|
| *G16C 20/30* | (2019.01) | |
| *G16C 20/70* | (2019.01) | |
| *G16C 20/80* | (2019.01) | |
| *G06N 3/02* | (2006.01) | |

(52) U.S. Cl.
CPC .............. *G16C 20/30* (2019.02); *G16C 20/70* (2019.02); *G16C 20/80* (2019.02); *G06N 3/02* (2013.01)

(58) Field of Classification Search
None
See application file for complete search history.

(56) References Cited

U.S. PATENT DOCUMENTS

| | | | | |
|---|---|---|---|---|
| 2006/0161407 A1* | 7/2006 | Lanza | ................. | G16B 20/00 703/11 |
| 2015/0134315 A1* | 5/2015 | Sarmiento | ............... | G16B 5/00 703/11 |
| 2019/0018933 A1* | 1/2019 | Oono | .................. | G06N 3/0454 |

FOREIGN PATENT DOCUMENTS

CN         103150490 A  *  6/2013

OTHER PUBLICATIONS

Summa et al., "An Atomic Environment Potential for use in Protein Structure Prediction" J. Mol. Biol. (2005) 352, 986-1001 (Year: 2005).*

(Continued)

*Primary Examiner* — John C Kuan
(74) *Attorney, Agent, or Firm* — Finnegan, Henderson, Farabow, Garrett & Dunner, LLP

(57) ABSTRACT

A computer-implemented method for predicting molecule properties is disclosed. According to some embodiments, the method may include receiving an input file of a compound. The method may also include implementing a neural network to determine molecular configurations of the compound based on the input file and a plurality of molecular descriptors associated with the compound. The method may also generating, using the neural network, one or more three-dimensional (3D) models of the compound based on the determined molecular configurations of the compound. The method may also include determining, using the neural network, energy scores of the one or more 3D models when the compound is docked into a protein. The method may further include determining a property of the docked compound based on the energy scores.

20 Claims, 13 Drawing Sheets

(56) References Cited

OTHER PUBLICATIONS

LeCun et al., "Deep learning" Nature, vol. 521, May 28, 2015 (Year: 2015).*
Ma et al., "Deep Neural Nets as a Method for Quantitative Structure-Activity Relationships" J. Chem. Inf. Model. 2015, 55, 263-274 (Year: 2015).*
Kearnes et al., "Molecular graph convolutions: moving beyond fingerprints" J Comput Aided Mol Des (2016) 30:595-608 (Year: 2016).*
Ramsundar et al., "Is Multitask Deep Learning Practical for Pharma?" J. Chem. Inf. Model. 2017, 57, 2068-2076 (Year: 2017).*
Huuskonen et al., "Aqueous Solubility Prediction of Drugs Based on Molecular Topology and Neural Network Modeling" J. Chem. Inf. Comput. Sci. 1998, 38, 450-456 (Year: 1998).*
Xu et al., "Demystifying Multitask Deep Neural Networks for Quantitative Structure-Activity Relationships" J. Chem. Inf. Model. 2017, 57, 2490-2504 (Year: 2017).*
Tayarani et al., "Artificial Neural Networks Analysis Used to Evaluate the Molecular Interactions between Selected Drugs and Human Cyclooxygenase2 Receptor" Iran J Basic Med Sci; 2013; 16: 1196-1202 (Year: 2013).*
Arakawa et al., "Application of the Novel Molecular Alignment Method Using the Hopfield Neural Network to 3D-QSAR" J. Chem. Inf . Comput. Sci. 2003, 43, 1396-1402 (Year: 2003).*

\* cited by examiner

- For each compound, Input:
  Smiles, property_1, property_2 ... property_n, descriptors or explicit features[optional]

| Sample | SMILES | Physical Description | Boiling point (°C) | Water Solubility (mg/L at 25°C) | pKow 25°C |
|---|---|---|---|---|---|
| | CC(=O)OC1=C C=CC=C1C(=O)O | Solid | 140 | 4600 | 3.49 |

Fig. 6

Compound Property Predictor
How It Works :
Graph convolution layers
Generate descriptor

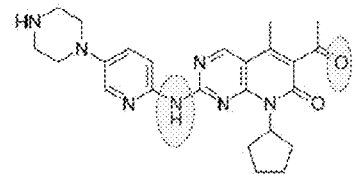

| Group Highlighted | Gcov Condition | After Convolution Layer 1 | After Convolution Layer 2 | After Convolution N |
|---|---|---|---|---|
| NH | Is a Atom N | Is connected with two carbon atoms and one hydrogen atom | Is connected with two element "C" which are on aromatic rings ... | Is in the middle of the compound as a "flexible linker", one side has property XXX, and other side has property YYY. |
| O | Is a Atom O | It connected with one carbon atom with double bound | Is one of the two "leaf nodes" of a Carbon atom | Is a tail of the compound, with nearest aromatic ring at distance 2 and XXXX |

Fig. 10

NEURAL NETWORK FOR PREDICTING DRUG PROPERTY

RELATED APPLICATIONS

This application claims priority from U.S. Provisional Patent Application No. 62/555,613, filed on Sep. 7, 2017, the entire contents of which are incorporated by reference in the present application.

TECHNICAL FIELD

The present disclosure generally relates to the technical field of computational biology and, more particularly, to a neural network for predicting drug properties.

BACKGROUND

Conventional drug discovery is a costly and lengthy process that typically involves large-scale compound screening or semi-rational design largely unguided by the structure or property information of the drug target. The challenges for structure-based drug design in part lie in how to accurately predict the actual conformations and properties of a given drug target. For example, a chemical compound may have a huge number of possible structures, and these structures may lead to different molecular properties, such as water solubility of the chemical compound. Accordingly, there is a need to develop a reliable and efficient method to accurately predict the conformations and properties of a potential drug compound. The disclosed methods and systems are directed to overcoming one or more of the problems and/or difficulties set forth above, and/or other problems of the prior art.

SUMMARY

According to certain aspects of the present disclosure, a computer-implemented method for predicting molecule properties is provided. The method may include receiving an input file of a compound. The method may also include implementing a neural network to determine molecular configurations of the compound based on the input file and a plurality of molecular descriptors associated with the compound. The method may also generating, using the neural network, one or more three-dimensional (3D) models of the compound based on the determined molecular configurations of the compound. The method may also include determining, using the neural network, energy scores of the one or more 3D models when the compound is docked into a protein. The method may further include determining a property the docked compound based on the energy scores.

It is to be understood that both the foregoing general description and the following detailed description are exemplary and explanatory only and are not restrictive of the invention, as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate embodiments consistent with the present disclosure and, together with the description, serve to explain the principles of the present disclosure.

FIG. 6 is a schematic diagram showing using descriptors of a knowing compound to train a neural network, according to an exemplary embodiment of the present disclosure.

FIG. 10 is a schematic diagram illustrating exemplary prediction results of compound properties generated by the neural network shown in FIG. 7, according to an exemplary embodiment of the present disclosure.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the present disclosure. Instead, they are merely examples of systems and methods consistent with aspects related to the invention as recited in the appended claims.

The features, aspects, and principles of the disclosed embodiments may be implemented in various environments. Such environments and related applications may be specifically constructed for performing the various processes and operations of the disclosed embodiments or they may include a general purpose computer or computing platform selectively activated or reconfigured by program code to provide the necessary functionality. The processes disclosed herein may be implemented by a suitable combination of hardware, software, and/or firmware. For example, the disclosed embodiments may implement general purpose machines that may be configured to execute software programs that perform processes consistent with the disclosed embodiments. Alternatively, the disclosed embodiments may implement a specialized apparatus or system configured to execute software programs that perform processes consistent with the disclosed embodiments.

The disclosed embodiments also relate to tangible and non-transitory computer readable media that include program instructions or program code that, when executed by one or more processors, perform one or more computer-implemented operations. For example, the disclosed embodiments may execute high level and/or low level software instructions, such as machine code (e.g., such as that produced by a compiler) and/or high level code that can be executed by a processor using an interpreter.

Figure 1:
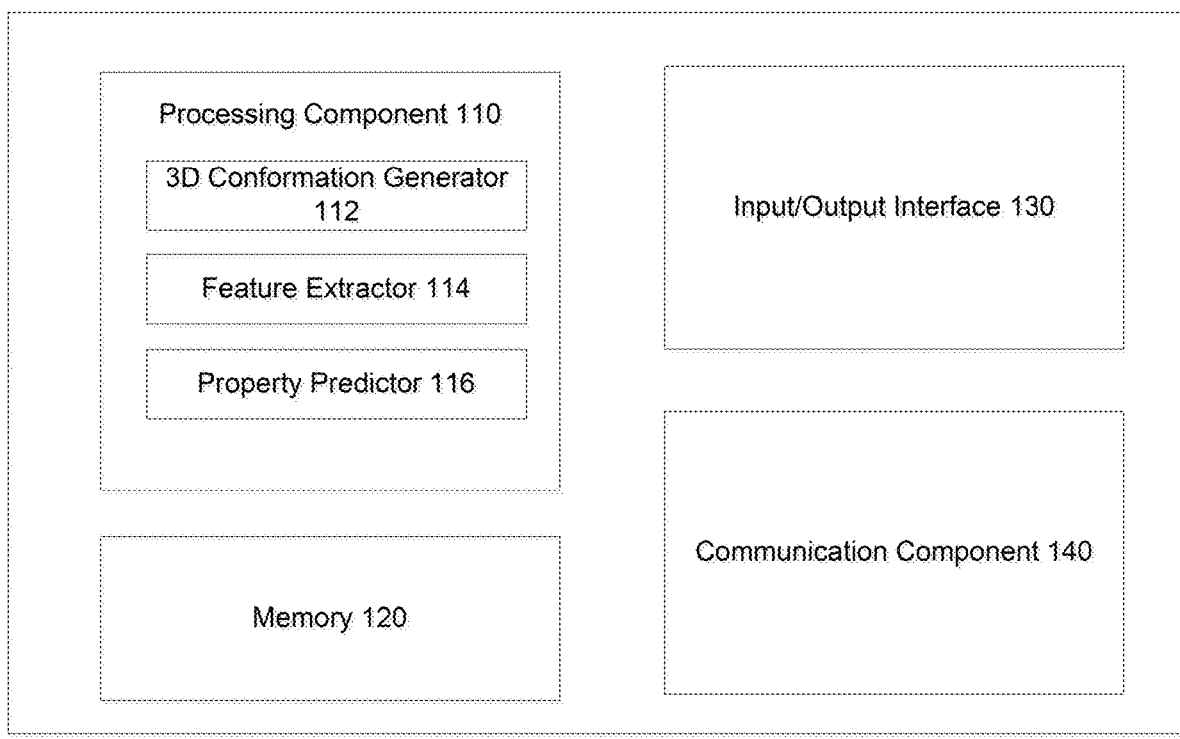
FIG. 1 is a block diagram of a system for predicting molecule properties, according to an exemplary embodiment of the present disclosure.

FIG. 1 is a block diagram of a system 100 for predicting molecule properties, according to an exemplary embodiment. For example, system 100 may be a desktop, a laptop, a server, a server cluster consisting of a plurality of servers, a cloud computing service center, etc. Referring to FIG. 1, system 100 may include one or more of a processing component 110, a memory 120, an input/out (I/O) interface 130, and a communication component 140.

Processing component 110 may control overall operations of device 100. For example, processing component 110 may include one or more processors that execute instructions to perform all or part of the steps in the following described methods. In particular, processing component 110 may include a three-dimensional (3D) conformation generator 112 configured to generate potential 3D conformations of a chemical compound based on two-dimensional (2D) structure, e.g., chemical formula and/or molecular descriptors, of the compound. Molecular descriptors are numerical values that characterize properties of molecules. For example, the molecular descriptors may be in the form of graph invariants. Moreover, processing component 110 may include a feature extractor 114 configured to employ a neural network to extract features of the 3D conformations generated by 3D conformation generator 112. Processing component 110 may further include a property predictor 116 configured to employ the neural network to predict properties, e.g., water solubility and pKa values, of the compound based on features extracted by feature extractor 114. Further, processing component 110 may include one or more modules (not shown) which facilitate the interaction between processing component 110 and other components. For instance, processing component 110 may include an I/O module to facilitate the interaction between I/O interface and processing component 110.

Processing component 110 may include one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing all or part of the steps in the above-described methods.

Memory 120 is configured to store various types of data and/or instructions to support the operation of device 100. Memory 120 may include a non-transitory computer-readable storage medium including instructions for applications or methods operated on device 100, executable by the one or more processors of device 100. For example, the non-transitory computer-readable storage medium may be a read-only memory (ROM), a random access memory (RAM), a CD-ROM, a magnetic tape, a memory chip (or integrated circuit), a hard disc, a floppy disc, an optical data storage device, or the like.

I/O interface 130 provides an interface between the processing component 110 and peripheral interface modules, such as input and output devices of device 100. I/O interface 130 may employ communication protocols/methods such as audio, analog, digital, serial bus, universal serial bus (USB), infrared, PS/2, BNC, coaxial, RF antennas, Bluetooth, etc. For example, I/O interface 130 may receive user commands from the input devices and send the user commands to processing component 110 for further processing.

Communication component 140 is configured to facilitate communication, wired or wirelessly, between system 100 and other systems/devices, such as devices connected to the Internet. Communication component 140 can access a wireless network based on one or more communication standards, such as Wi-Fi, LTE, 2G, 3G, 4G, 5G, etc. In some embodiments, communication component 140 may be implemented based on a radio frequency identification (RFID) technology, an infrared data association (IrDA) technology, an ultra-wideband (UWB) technology, a Bluetooth (BT) technology, or other technologies. For example, communication component 140 may access data regarding the chemical compound via the Internet and/or send the prediction results to a user.

Figure 2:
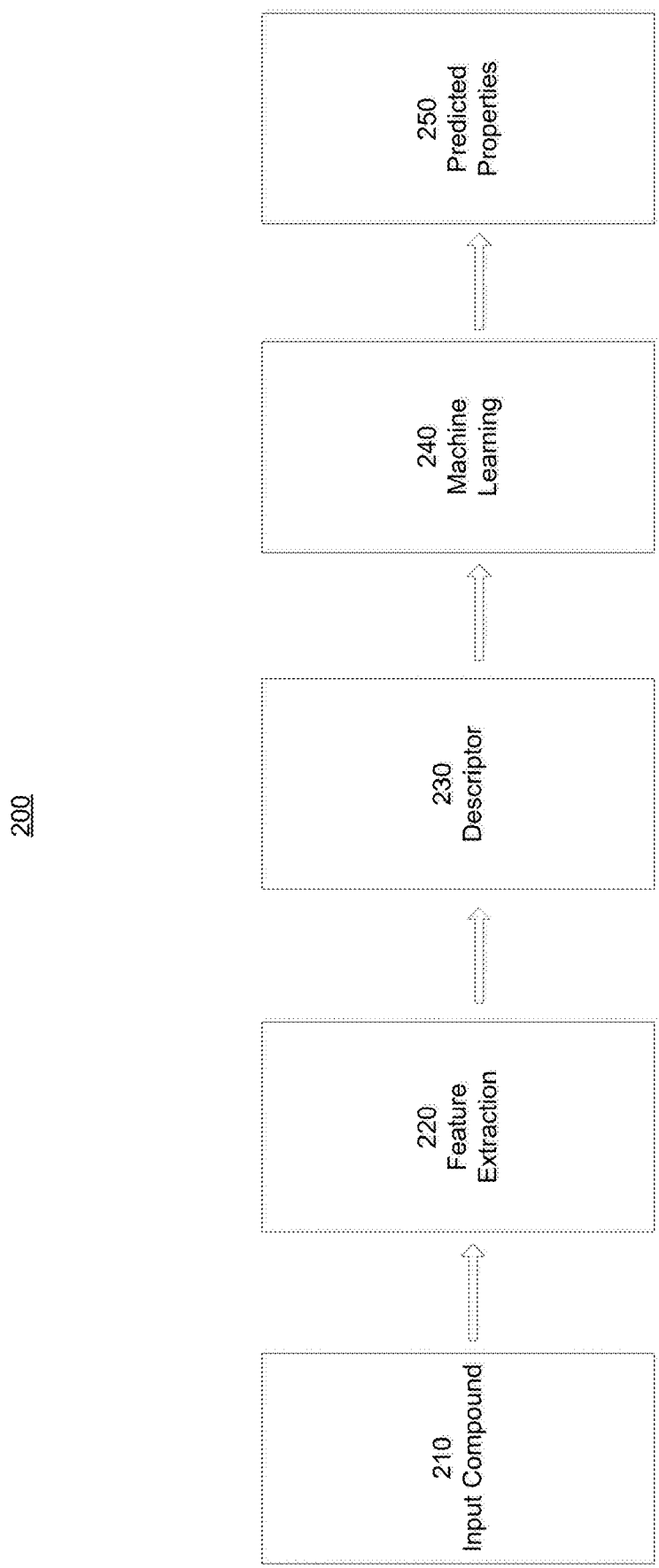
FIG. 2 is a schematic diagram illustrating a process for predicting molecule properties, according to an exemplary embodiment of the present disclosure.

FIG. 2 is a schematic diagram illustrating a process 200 for predicting molecule properties, according to an exemplary embodiment of the present disclosure. Process 200 may be performed by system 100 (particularly processing component 110) to predict the properties of a compound. Referring to FIG. 2, process 200 may include the following steps.

At step 210, processing component 110 receives input regarding the compound information, such as the compound's chemical formula. To be used by system 100, the input must be quantized. The input of the system may be, for example, structural information regarding a small molecule, a ligand, a ligand-receptor complex, etc. The protein structural information used in the disclosed embodiments may be extracted from the Protein Data Bank (PDB) data, which may be organized in various file formats, such as PDB file format, Extensible Markup Language (XML) file format, or macromolecular Crystallographic Information File (mmCIF) format. For illustrative purpose only, this disclosure assumes the PDB data is represented as PDB files. However, it is contemplated that the PDB data used by the disclosed methods may be represented in any format.

At step 220, processing component employs a neural network to extract features of the compound. A deep neural network capable of extracting and learning some important chemical features is disclosed in U.S. application Ser. No. 15/591,075, filed May 9, 2017, published as U.S. Patent Publication No. 2017-0329892, hereby incorporated by reference. The deep neural network was able to predict the amino acid side chain conformation, outperforming the standard method, SCWRL4, by over 25% across amino acid types.

The neural network may be employed to construct one or more feature vectors for the input compound. In certain embodiments, the constructed feature vectors comprise a dense feature vector for each atom of the compound, wherein each dense feature vector includes the features of an atom and features of the interaction between that atom and another atom.

The neural network may include layers for quantifying the input information regarding the compound. The quantization of the input may be conducted in a variety of ways. Processing component 110 may derive quantized information on the input compound based on its chemical formula, a chemical name, a high-resolution image of the crystal structure, a chemical drawing, data about the molecule, data about the atoms comprising the molecule, data about atom interactions, or any other method known to one of ordinary skill in the art for providing information to the system regarding the structure of the molecule (e.g., the type of atom and the other atoms to which each atom is bonded).

In an exemplary embodiment, the inputs are quantized as dense feature vectors for each atom and atom pair. The dense feature vectors may take the form of $A_a$, $P_{(a,b)}$, with $A_a$ defined as the feature vector of atom a, and $P_{(a,b)}$ defined as the feature vector of atom pair a and b.

Table 1 provides a list of exemplary atom features that may comprise a feature vector for atom a. Typical atom features include atom type, atom radius, and whether the atom is in an aromatic ring.

TABLE 1

| Atom feature | Description | Size |
|---|---|---|
| Atom type | One hot vector specifying the type of this atom. | 23 |
| Radius | van der Waals radius and covalent radius of the atom. | 2 |
| In rings | For each size of ring (3-8), the number of rings that include this atom. | 6 |
| In aromatic ring | Whether this atom is part of an aromatic ring | 1 |
| Pairwise potential | Sum of pairwise atom potential between this atom and receptor atoms. | 1 |

As shown in Table 1, in exemplary embodiments, the type of atom may be provided to the system by entering one value (i.e., one hot vector), wherein each value corresponds to an atom type, such as the 23 atom types detailed Table 1 a. Atom types are essential for ranking the potential energies of the possible side chain conformations. The disclosed embodiments presume that atoms with the same electronic, chemical, and structural properties share the same atom type, and classify each atom by its neighboring atoms and bonds.

Several strategies have been developed in the related art to define the atom types, such as the strategies described in, e.g., Summa C M, Levitt M, DeGrado W F, An atomic environment potential for use in protein structure prediction, *Journal of Molecular Biology* (2005) 352(4): 986-1001; or the CHARMM force field (see www.charmm.org). These strategies are incorporated in the present disclosure by reference.

Figure 3:
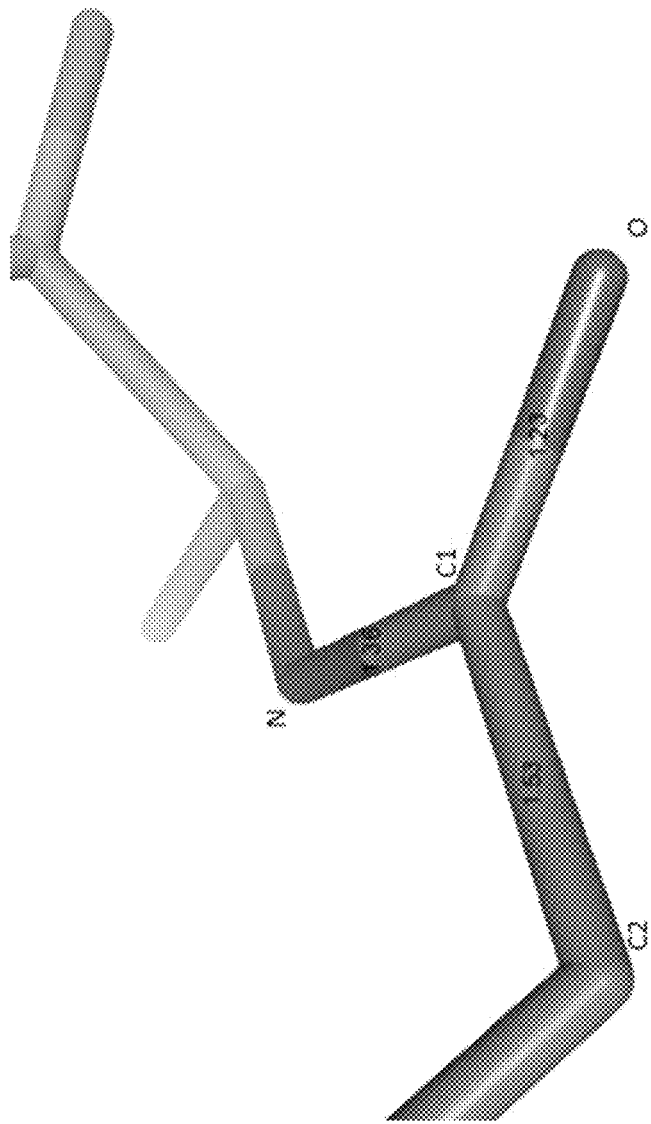
FIG. 3 is a schematic diagram illustrating a local structure of an amino acid side chain, according to an exemplary embodiment of the present disclosure.

In addition, the present disclosure provides the following method for generating the atom types:

1. Extract information regarding the bond environment of each atom in the amino acids of a protein. The bond environment may include: the element of the atom at question, the bond lengths of the atom at question, and the elements of the atoms bonding with the atom at question. For example, FIG. 3 is a schematic diagram illustrating a local structure of an amino acid side chain. Referring to FIG. 3, the bond environment for atom C1 may be presented as: (C, (1.23, 1.36, 1.53)). That is, the element of the atom at question is carbon. The atom's bond lengths are 1.23 Å, 1.36 Å, and 1.53 Å, respectively.
2. Classify the atoms into one or more clusters according to the atoms' bond environments. The atoms in the same cluster have similar bond environments. Any of the above-described clustering methods, e.g., K-means clustering method or spectral clustering method, may be used to classify the atoms.
3. Assign a unique atom type to each cluster.

In one embodiment, atoms found in the 20 common amino acids are classified into 23 atom types, using the above-describe method. Any unclassified atoms are classified as "unknown atom type."

As indicated in Table 1a, certain embodiments may only require information on non-hydrogen atoms (e.g., various types of carbon, oxygen, nitrogen, and sulfur), and individual hydrogen may not be considered and/or information about hydrogen atoms may not be entered into the system. In certain embodiments, information about the hydrogen atoms in the molecule may be derived from and/or assumed by the system based on the types of non-hydrogen atoms present in the molecule.

TABLE 1a

| Type | Atoms |
|---|---|
| 1 | ALA C; ARG C; ASN C; ASN CG; ASP C; CYS C; GLN C; GLN CD; GLU C; GLY C; HIS C; ILE C; LEU C; LYS C; MET C; PHE C; PRO C; SER C; THR C; TRP C; TYR C; VAL C; |
| 2 | ALA $C^\alpha$; ARG $C^\alpha$; ASN $C^\alpha$; ASP $C^\alpha$; CYS $C^\alpha$; GLN $C^\alpha$; GLU $C^\alpha$; HIS $C^\alpha$; ILE $C^\alpha$; LEU $C^\alpha$; LYS $C^\alpha$; MET $C^\alpha$; PHE $C^\alpha$; PRO $C^\alpha$; SER $C^\alpha$; THR $C^\alpha$; THR $C^\alpha$; TRP $C^\alpha$; TYR $C^\alpha$; VAL $C^\alpha$; |
| 3 | ALA $C^\beta$; ILE $C^\delta_1$; ILE $C^\gamma_2$; LEU $C^\delta_1$; LEU $C^\delta_2$; THR $C^\gamma_2$; VAL $C^\gamma_1$; VAL $C^\gamma_2$; |
| 4 | ALA N; ARG N; ARG $N^\epsilon$; ASN N; ASP N; CYS N; GLN N; GLU N; GLY N; HIS N; ILE N; LEU N; LYS N; MET N; PHE N; SER N; THR N; TRP N; TYR N; VAL N; |
| 5 | ALA O; ARG O; ASN O; ASN $O^\delta_1$; ASP O; ASP $O^\delta_1$; ASP $O^\delta_2$; CYS O; GLN O; GLN $O^\epsilon_1$; GLU O; GLU $O^\epsilon_1$; GLU $O^\epsilon_2$; GLY O; HIS O; ILE O; LEU O; LYS O; MET O; PHE O; PRO O; SER O; THR O; TRP O; TYR O; VAL O; |
| 6 | ARG $C^\beta$; ARG $C^\gamma$; ASN $C^\beta$; ASP $C^\beta$; GLN $C^\beta$; GLN $C^\gamma$; GLU $C^\beta$; GLU $C^\gamma$; HIS $C^\beta$; ILE $C^\gamma_1$; LEU $C^\beta$; LYS $C^\beta$; LYS $C^\delta$; LYS $C^\epsilon$; LYS $C^\gamma$; MET $C^\beta$; PHE $C^\beta$; PRO $C^\beta$; PRO $C^\delta$; PRO $C^\gamma$; TRP $C^\beta$; TYR $C^\beta$; |
| 7 | ARG $C^\delta$; GLY $C^\alpha$; SER $C^\beta$; |
| 8 | ARG $C^\zeta$; |
| 9 | ARG $N^\eta_1$; ARG $N^\eta_2$; ASN $N^\delta_2$; GLN $N^\epsilon_2$; |

TABLE 1a-continued

| Type | Atoms |
|---|---|
| 10 | ASP $C^\gamma$; GLU $C^\delta$; |
| 11 | CYS $C^\beta$; MET $C^\gamma$; |
| 12 | CYS $S^\gamma$; |
| 13 | HIS $C^\delta{}_2$; HIS $C^\epsilon{}_1$; PHE $C^\delta{}_1$; PHE $C^\delta{}_2$; PHE $C^\epsilon{}_1$; PHE $C^\epsilon{}_2$; PHE $C^\zeta$; TRP $C^\delta{}_1$; TRP $C^\epsilon{}_3$; TRP $C^\eta{}_2$; TRP $C^\zeta{}_2$; TRP $C^\zeta{}_3$; TYR $C^\delta{}_1$; TYR $C^\delta{}_2$; TYR $C^\epsilon{}_1$; TYR $C^\epsilon{}_2$; |
| 14 | HIS $C^\gamma$; PHE $C^\gamma$; TYR $C^\gamma$; |
| 15 | HIS $N^\delta{}_1$; HIS $N^\epsilon{}_2$; TRP $N^\epsilon{}_1$; |
| 16 | ILE $C^\beta$; LEU $C^\gamma$; VAL $C^\beta$; |
| 17 | LYS $N^\zeta$; |
| 18 | MET $C^\epsilon$; |
| 19 | MET $S^\delta$; |
| 20 | PRO N; |
| 21 | SER $O^\gamma$; THR $O^\gamma{}_1$; TYR $O^\eta$; |
| 22 | TRP $C^\delta{}_2$; TRP $C^\epsilon{}_2$; TYR $C^\zeta$; |
| 23 | TRP $C^\gamma$; |

As shown in exemplary Table 1, in certain embodiments, two values may be entered for the atom radius: (1) the van der Waals radius, and (2) the covalent radius of the atom.

As shown in exemplary Table 1, in certain embodiments, information on both the size and number of rings to which the atom belongs is entered. For example, a single atom may be part of 1 ring of 5 atoms and 1 ring of 6 atoms.

As shown in exemplary Table 1, in certain embodiments, information on whether the atom is part of an aromatic ring may be entered.

As shown in exemplary Table 1, in certain embodiments, a value representing the sum of the pairwise atom potential between the atom and protein receptor atoms may be entered. Details regarding the calculation of pairwise potentials may be found in U.S. application Ser. No. 15/591,075, filed May 9, 2017, which is hereby incorporated by reference in its entirety.

In brief, a scoring function H(x) may be applied to a ligand atom and a receptor atom to obtain a score representing the interaction for that pair of atoms. All interactions between the ligand atom and potentially many receptor atoms are scored using the H(x) function. The sum of these scores is the pairwise potential of that ligand atom. The H(x) function may be developed by machine learning algorithms, such as the H(distance, anglescore) function described below.

The pairwise potential score may be used in multiple steps in the process. For example, the ligand's pairwise potential score may be used as a weak scoring function in the anchor and grow process for the initial sampling of ligand poses. In the neural network model, the pairwise potential score of an atom may be used as one feature for each atom, as shown in the last row of Table 1, above.

An atom's pairwise potential relates to forces between that atom and atoms of the receptor protein, such as van der Waals force and electrostatic force. The force between two atoms is determined by the type of the atoms, the distances between the atoms, and the angle between the force and the bonds of the atoms. For example, traditional force field methods, including CHARMM, use several type of pairwise potentials, such as Lennard-Jones and electrostatic terms.

In some embodiments, different terms of the atom pairwise potential may be merged. For example, if the atom pairwise potential includes a term $F_1$ expressed in $F_1$(distance), a term $F_2$ expressed in $F_2$(distance), then a new term F may be defined according to: F(distance)=$F_1$(distance)+ $F_2$(distance). Therefore, any number of explicit pairwise energy functions can be merged to a single implicit scoring function H(x), which may be the H(distance, anglescore) function introduced below. This way, the pairwise potential is described by implicit potential terms instead of explicit potential terms.

Figure 4:
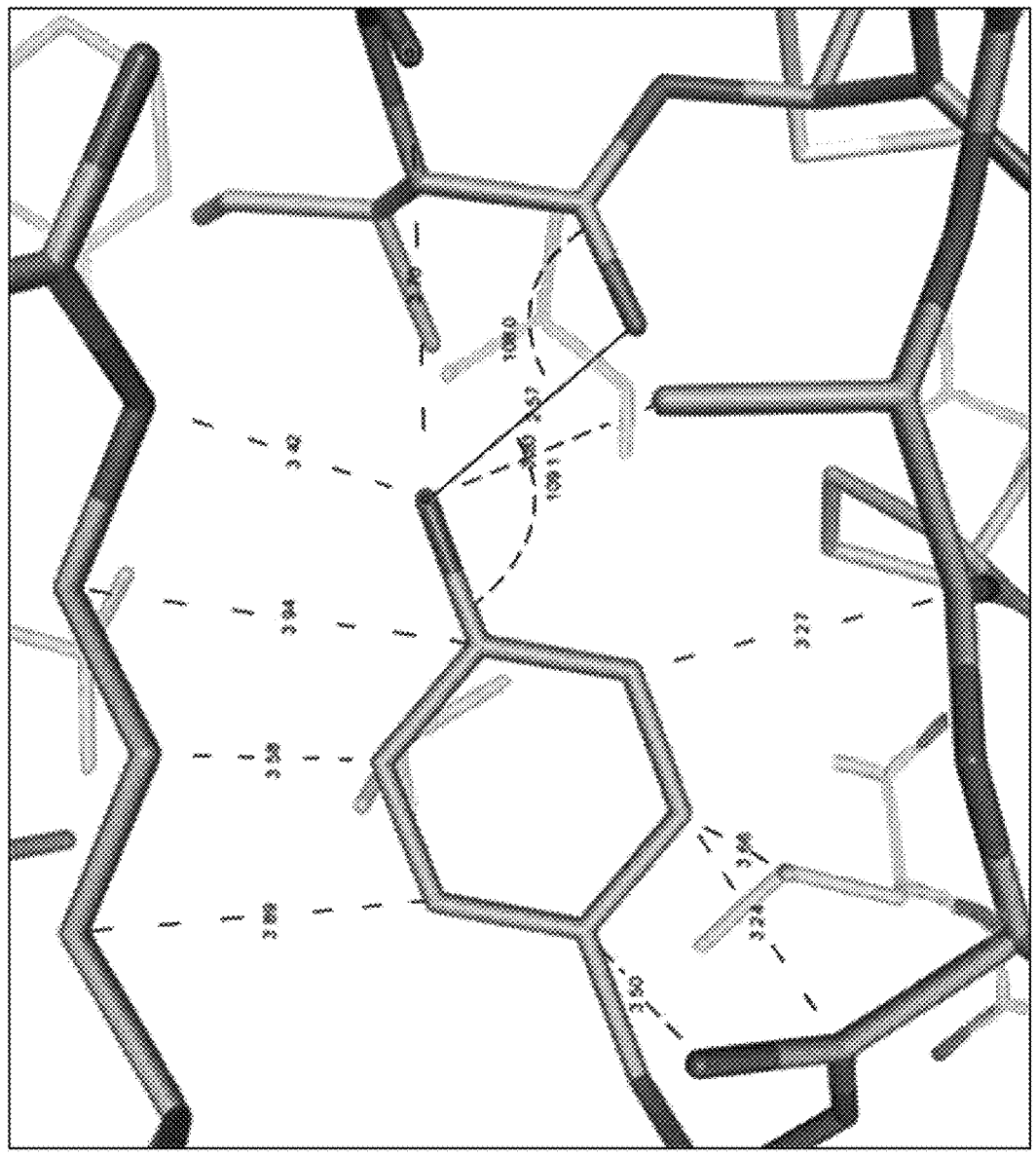
FIG. 4 is a schematic diagram illustrating pairwise interaction between two atoms, according to an exemplary embodiment of the present disclosure.

Besides distances between the atoms, the pairwise potential also depends on the direction of the pairwise interactions between the atoms. The direction is particularly important in the cases involving polar atoms. Generally, bonded atoms contributed more to the pairwise potential than non-bonded atoms. FIG. 4 is a schematic diagram illustrating pairwise interaction between two atoms. Referring to FIG. 4, the distance between two oxygen atoms (identified as 1601 and 1602) is 2.57 Å, and the angles between the pairwise force vector and the bonds associated with the two oxygen atoms are 109.1° and 108.0°, respectively. An angle score may be defined to measure the influence of the bonds on the pairwise potential. The angle score is the dot product between an atom's pairwise force vector and bond vector. For an atom with more than one covalent bond, the dot product is between the atom's pairwise force vector and the sum of all the bond vectors. The angle score may be normalized and thus have a range of [−1,1].

Figure 5B:
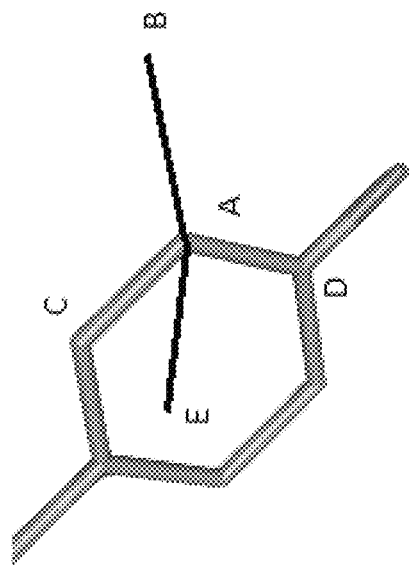
FIG. 5b is a schematic diagram illustrating multiple pairwise interactions associated with an atom that has two covalent bonds, according to an exemplary embodiment of the present disclosure.
Figure 5A:
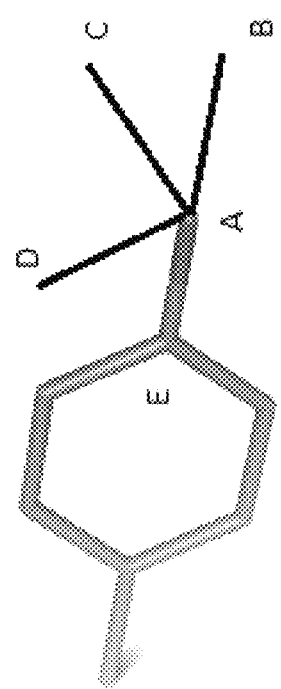
FIG. 5a is a schematic diagram illustrating multiple pairwise interactions associated with an atom that has a covalent bond, according to an exemplary embodiment of the present disclosure.

FIG. 5a is a schematic diagram illustrating multiple pairwise interactions associated with an atom that has a covalent bond. Referring to FIG. 5a, the oxygen atom A has only one covalent bond. The covalent bond is represented by the vector $\overrightarrow{EA}$. An angle score of atom A may be defined as the dot product between a pairwise force vector associated with atom A and the bond vector EA. For example, the pairwise interaction formed between atom A and atom B has the highest possible angle score, since $\overrightarrow{EA} \cdot \overrightarrow{AB}=1$. Conversely, the pairwise interaction formed between atom A and atom E has the lowest angle score since $\overrightarrow{EA} \cdot \overrightarrow{AE}=-1$. Moreover, the pairwise interactions formed between atom A and atom C or D have an angle score in between −1 and 1.

FIG. 5b is a schematic diagram illustrating multiple pairwise interactions associated with an atom that has two covalent bonds. Referring to FIG. 5b, atom A has two bond vectors $\overrightarrow{CA}$ and $\overrightarrow{DA}$. The pairwise interaction formed between atom A and atom B has a pairwise force vector AB, which is in the same direction as the net vector $\overrightarrow{CA}+\overrightarrow{DA}$. Accordingly, the pairwise interaction formed between atom A and atom B has the highest angle score. Conversely, pairwise force vector AE is in the opposite direction of the net vector $\overrightarrow{CA}+\overrightarrow{DA}$, and thus the pairwise interaction formed between atom A and atom E has the lowest angle score. For atoms with more than two covalent bonds, the angle score is similarly defined.

After the distances and angle scores are determined, the atom pairwise potential energy may be determined. For each pair of atoms in a certain molecular environment, there may be a unique function H(distance, anglescore) based on atom types and molecular environments of both atoms. The unique H(distance, anglescore) for the pair of atoms may be trained using machine learning algorithms. For example, H(distance, anglescore) may equal $\vec{W} \cdot \vec{F}$, where $(x_1, x_2, x_3, \ldots, x_n)$ is the feature vector $\vec{F}$ for the correct pairwise interaction (i.e., the distance and angle for the pair of atoms in the conformation to be predicted), $(y_1, y_2, y_3, \ldots y_n)$ is the feature vector for the incorrect pairwise interaction, and weight vector $\vec{W} = (w_1, w_2, w_3, \ldots, w_n)$. The weight factor $\vec{W}$ may be obtained such that $(\Sigma_{i=1}^{n} w_i x_i - \Sigma_{i=1}^{n} w_i y_i) > 0$. This way, the feature vector with the highest $\vec{W} \cdot \vec{F}$ corresponds to the pairwise interaction that is most energy favorable. The pairwise interactions with higher energy scores are more likely to occur in reality.

In exemplary embodiments, a machine-learning algorithm may be used to train the weight vector $\vec{W}$. The training data may be obtained from real-world protein structure data, such as Protein Database (PDB) files from the Research Collaboratory for Structural Bioinformatics (RCSB). For example, correct feature vectors may be constructed for the conformations shown in the PDB files and additional, incorrect conformations may be constructed. A machine-learning algorithm, e.g., a linear regression process, may then be executed to search for the $\vec{W}$ satisfying the equation $(\Sigma_{i=1}^{n} w_i x_i - \Sigma_{i=1}^{n} w_i y_i) > 0$.

As explained above, the scoring function H(distance, anglescore) may be used to calculate a pairwise potential energy score of the interaction of both atoms. Then all interactions consisting of a certain atom may be summed to provide a single pairwise potential energy feature for that particular atom.

Table 2 provides a list of exemplary atom pair features that may comprise a feature vector of atom pair a,b. Typical atom pair features include the inter-atomic distance and the bonding factors between two atoms.

TABLE 2

| Pair feature | Description | Size |
| --- | --- | --- |
| Bond type | One hot vector of {Single, Double, Triple} or null. | 3 |
| Distance | Distance of this atom pair. | 1 |
| Same ring | Whether the atoms are in the same ring. | 1 |

As shown in exemplary Table 2, in certain embodiments, a value indicating whether the bond between atom pair a and b is a single, double, or triple bond may be entered. A value indicating the distance between atoms a and b may also be entered. An indication that the two atoms are part of the same ring may also be entered.

Again, the dense feature vectors for the atoms and atom pairs of the ligand disclosed above are merely examples of information that may be provided to the system. One of ordinary skill in the art would understand suitable molecule description information to provide as quantized input to the system based at least on this disclosure.

Through this quantization process, the ligand may be represented by the quantized data. In an exemplary embodiment, the ligand may be represented by an unordered set of atom features $(A_a, A_b, \ldots A_n)$ and atom pair features $(P_{a,b}, P_{a,c}, \ldots P_{n-1,n})$.

At step 230, processing component 110 may also allow a user to self-define molecular descriptors of the compound and/or obtain molecular descriptors from other sources, e.g., commercial databases, and use these molecular descriptors to extract the features of the compound.

At step 240, processing component 110 may employ a machine learning algorithm to predict the molecular configurations of the input compound. The machine-learning algorithm, e.g., a regression process, may use the feature vectors (from step 220) and descriptors (from step 230) to train a prediction model for predicting the most appropriate conformation for a side chain. Specifically, features relating to the potential energy of each molecular configuration of the compound may be extracted and used to form a feature vector representative of the respective molecular configuration. Sample feature vectors are used to train the prediction model, such that the model may be used to compute the energy scores of molecular configurations. The molecular configurations with the highest energy score are the most appropriate configurations for the compound.

At step 250, processing component 110 may predict properties of the compound based on the predicted molecular configurations. In the disclosed embodiments, the properties of the compound may include water solubility, pKa values, equilibrium dissociation constants (KD), inhibitor constant (Ki) docking pose rankings, etc. The properties may also include ADMET (absorption, distribution, metabolism, excretion, and toxicity) properties of the compound.

For example, one particular use case of the disclosed system and method is to predict ligand docking poses, i.e., the preferred conformation and orientation of a small molecule when bound to a protein, as disclosed in U.S. application Ser. No. 15/984,129, filed May 18, 2018, hereby incorporated by reference.

FIG. 6 is a schematic diagram showing using descriptors of a known compound to train a neural network, according to an exemplary embodiment. As shown in FIG. 6, the neural network may be trained using input data of known compounds. For example, the training data may include chemical formula, physical description, boiling point, water solubility, and pKa value of a known compound. The training data may be expressed as (compound name, property_1, property_2, . . . , property n). The property_1, property_2, . . . , property n are descriptors associated with the compound, and can be input by a user of drawn from a database.

Figure 7:
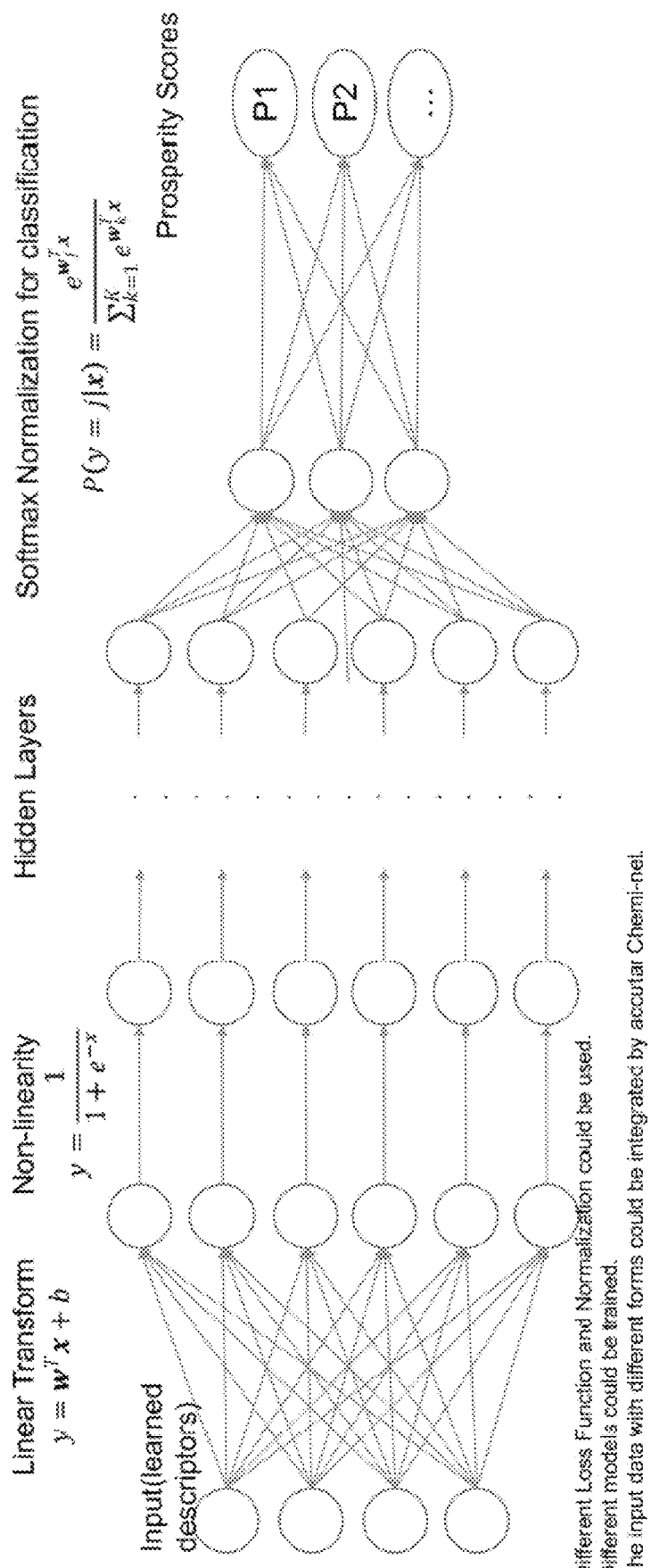
FIG. 7 is a schematic diagram illustrating the structures, e.g., layer structure, of an exemplary neural network employed by the disclosed neutral network system.
Figure 8:
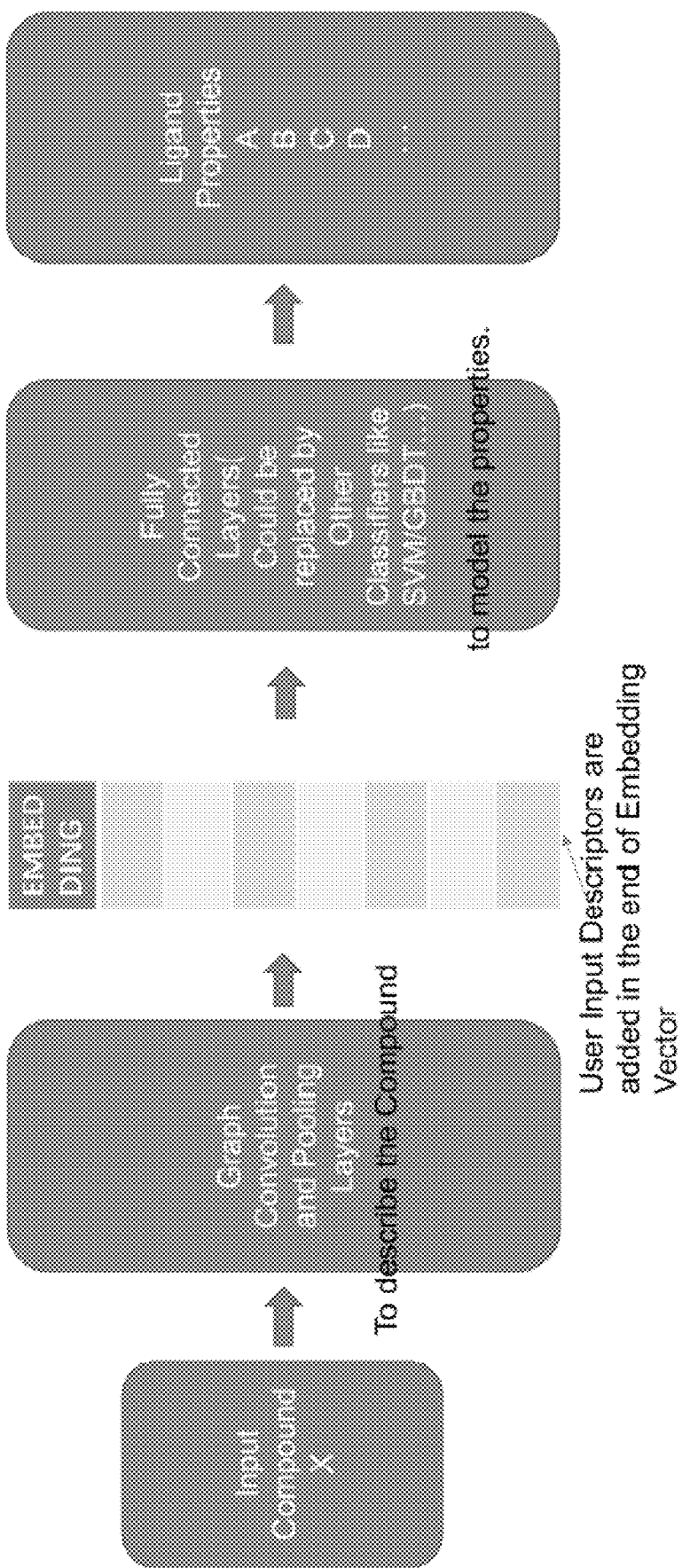
FIG. 8 is a schematic diagram illustrating implementing process 200 using the neural network shown in FIG. 7, according to an exemplary embodiment of the present disclosure.
Figure 9:
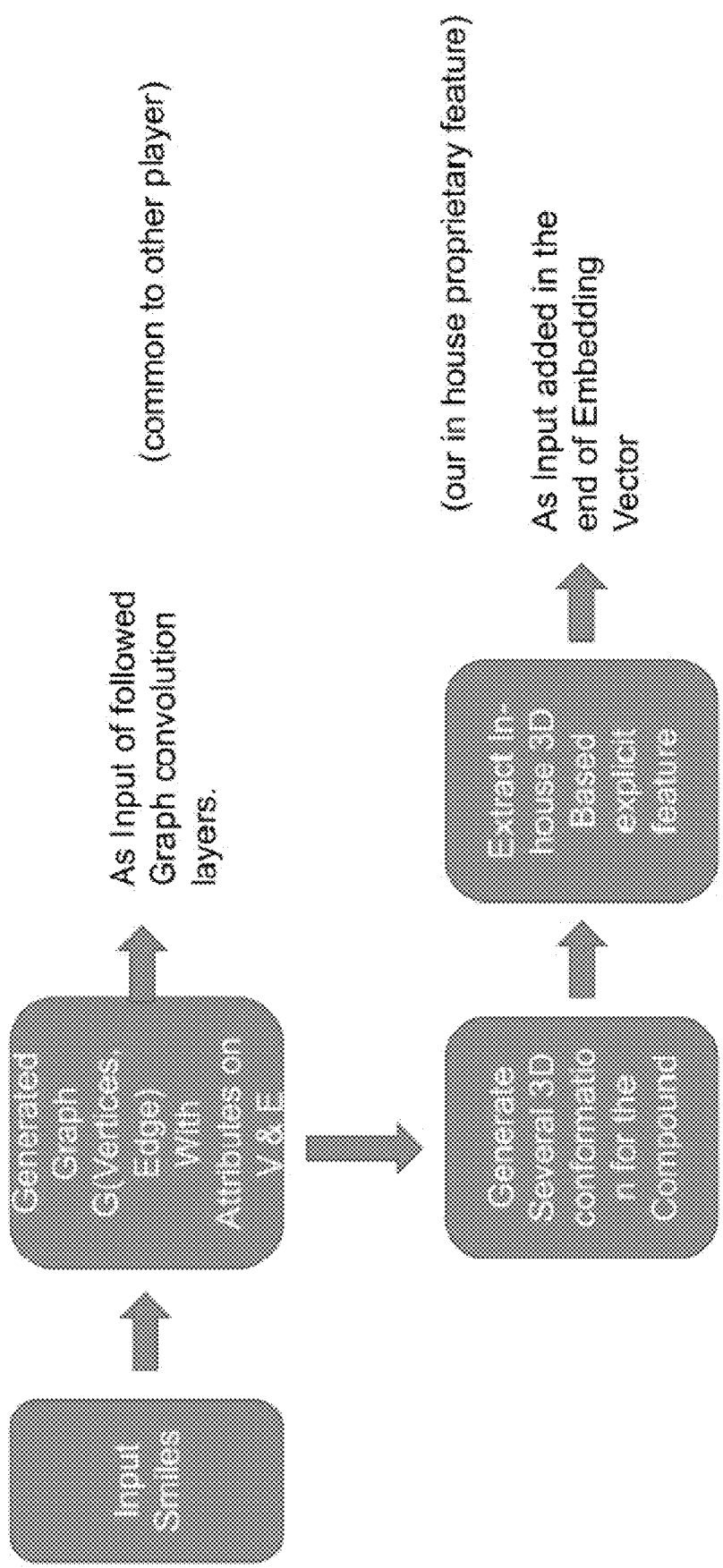
FIG. 9 is a schematic diagram illustrating a process for performing input quantization using the neural network shown in FIG. 7, according to an exemplary embodiment of the present disclosure.

FIGS. 7-10 illustrate certain implementations of the disclosed neural network. FIG. 7 is a schematic diagram illustrating the structures, e.g., layer structure, of an exemplary neural network employed by the disclosed neutral network system. FIG. 8 is a schematic diagram illustrating implementing process 200 using the neural network shown in FIG. 7. FIG. 9 is a schematic diagram illustrating a process for performing input quantization using the neural network shown in FIG. 7. In some embodiments, the neural network is configured to generate one or more 3D models of the compound based on 2D data, e.g., chemical formula and/or molecular descriptors, of the compound. FIG. 10 is a schematic diagram illustrating exemplary prediction results of compound properties generated by the neural network shown in FIG. 7.

Figure 11:
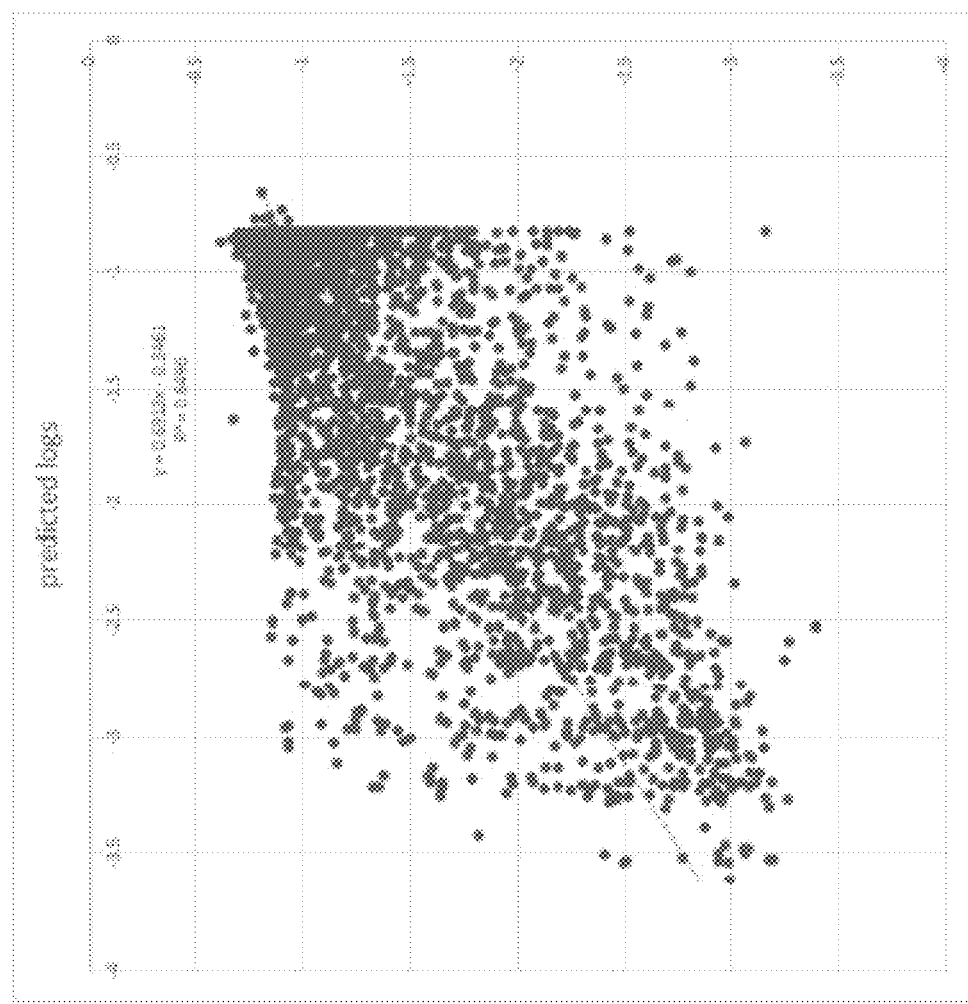
FIG. 11 illustrates predicted solubility of a compound generated by the disclosed neural network system.

FIG. 11 illustrates predicted solubility of a compound generated by the disclosed neural network system. By comparing to the measured solubility data, the solubility predicted using the disclosed neural network system is superior to those predicted by existing method.

Figure 12:
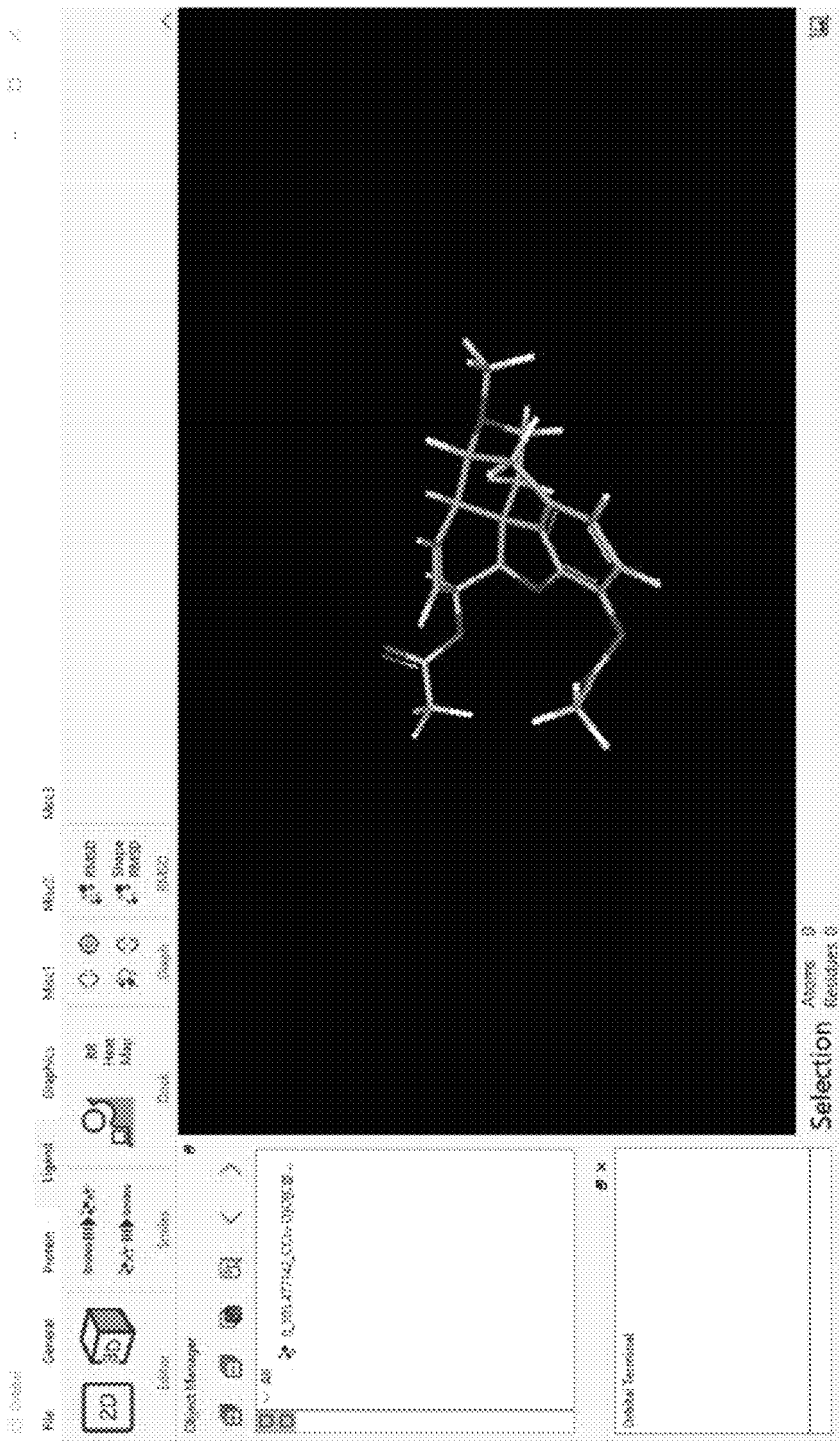
FIG. 12 illustrates 3D conformations of a heroin molecule generated by the disclosed neural network system.

FIG. 12 illustrates 3D conformations of Heroin molecule generated by the disclosed neural network system.

Figure 13:
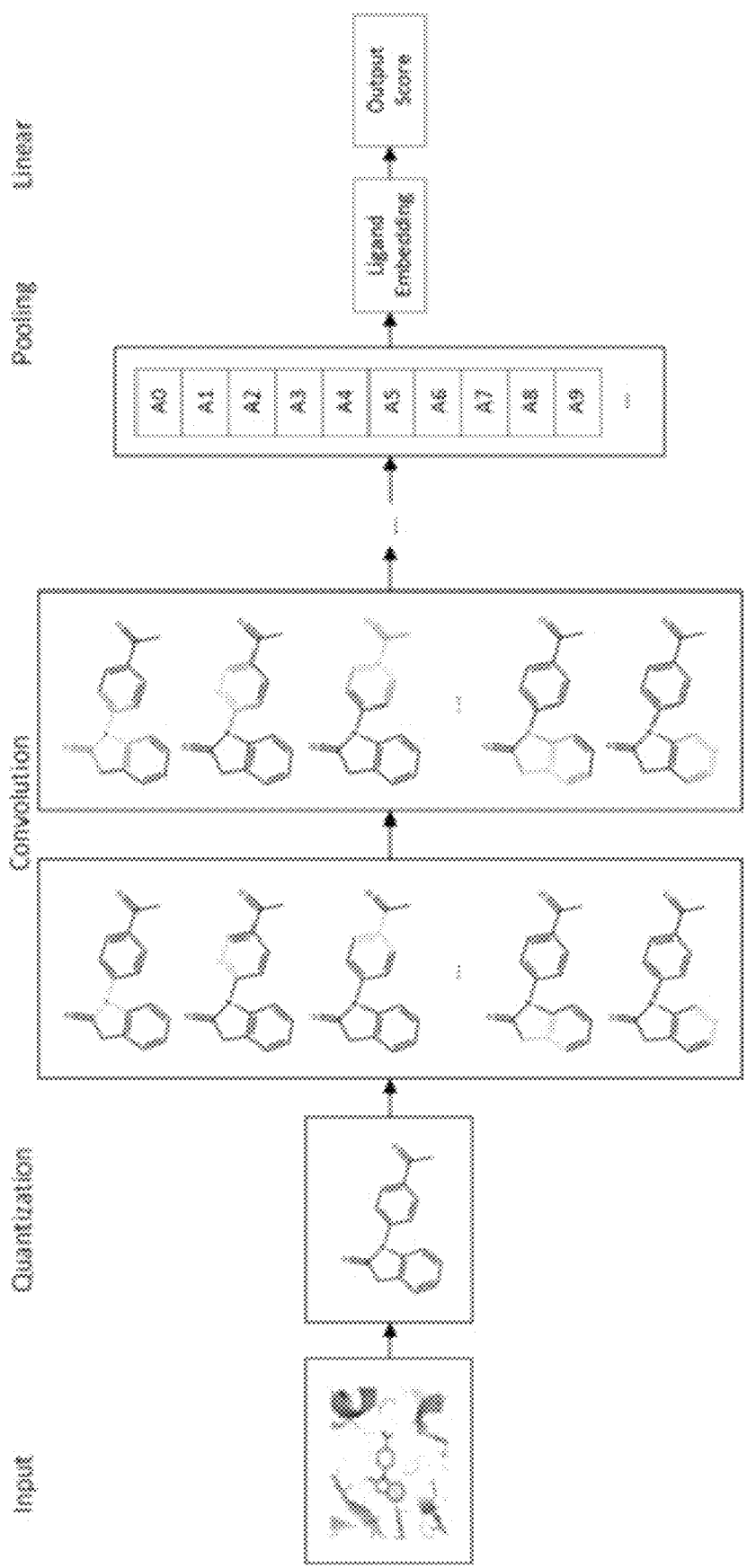
FIG. 13 is a schematic diagram illustrating implementing the disclosed neutral network to predict ligand docking poses, according to an exemplary embodiment of the present disclosure.

FIG. 13 is a schematic diagram illustrating implementing the disclosed neutral network to predict ligand docking poses. As shown in FIG. 13, the deep neural network accepts a sampled receptor-ligand complex that is quantized using inputs include a static pairwise potential score system, and it outputs the probability or feasibility score of a given ligand pose or conformational structure.

As shown in FIG. 13, after the input atom and atom pair features are quantized for each atom in the ligand, the feature vectors are fed through a series of graph-based convolution operators. The convolution process is described in more detail below. Each convolution operation transforms the dense feature vectors and assigns weights to them. The set of dense feature vectors that result from the convolution process are reduced to a single dense feature vector, called a feature map, which is further transformed through several fully connected layers to obtain a final feasibility score for the ligand's conformation.

The final feasibility score can then be used to rank the various ligand conformations and/or otherwise predict the binding of the ligand/protein complex. The detailed description of the using disclosed neural network to predict the ligand docking poses can be found in U.S. application Ser. No. 15/984,129, filed May 18, 2018, the entire contents of which are incorporated by reference.

This application is intended to cover any variations, uses, or adaptations of the present disclosure following the general principles thereof and including such departures from the present disclosure as come within known or customary practice in the art. Other embodiments of the present disclosure will be apparent to those skilled in the art from consideration of the specification and practice of the present disclosure. It is intended that the specification and examples be considered as exemplary only, with a true scope and spirit of the invention being indicated by the following claims.

In particular, variations of the disclosed methods will be apparent to those of ordinary skill in the art, who may rearrange and/or reorder the steps, and add and/or omit certain steps without departing from the spirit of the disclosed embodiments. Non-dependent steps may be performed in any order, or in parallel.

Consistent with the present disclosure, the following description is about an embodiment in which the disclosed methods are applied to predict amino acid side chain using a deep neural network.

What is claimed is:

1. A computer-implemented method for predicting molecule properties, the method comprising:
   determining a plurality of molecular descriptors associated with a first compound;
   determining one or more three-dimensional (3D) conformations of the first compound;
   training a neural network using a training set comprising:
      the plurality of molecular descriptors associated with the first compound, and
      the one or more 3D conformations of the first compound,
      wherein training the neural network comprises determining a plurality of features that affect energies of the one or more 3D conformations of the first compound;
   receiving an input file of a second compound;
   implementing the neural network to determine, based on the input file and a plurality of molecular descriptors associated with the second compound, molecular configurations of the second compound docketed in a protein;
   generating, using the neural network, one or more 3D models of the second compound based on the determined molecular configurations of the second compound;
   determining, using the neural network, energy scores of the one or more 3D models; and
   determining, using the neural network, a property of the docked second compound based on the energy scores.

2. The method of claim 1, wherein the property includes at least one of water solubility, pKa value, equilibrium dissociation constant (KD), inhibitor constant (Ki), docking pose ranking, absorption property, distribution property, metabolism property, excretion property, or toxicity of the second compound.

3. The method of claim 1, wherein implementing the neural network to determine the molecular configurations of the second compound docketed in the protein comprises:
   extracting features associated with the molecular configurations of the second compound docketed in the protein; and
   constructing, based on the extracted features, feature vectors associated with the molecular configurations of the second compound.

4. The method of claim 3, wherein determining, using the neural network, the energy scores of the one or more 3D models comprises performing at least one convolution of the feature vectors associated with the molecular configurations of the second compound.

5. The method of claim 1, wherein determining, using the neural network, the energy scores of the one or more 3D models comprises applying a scoring function to feature vectors of atoms of the second compound for each of the molecular configurations.

6. The method of claim 5, wherein the scoring function is a weighted scoring function that applies a weighted vector to the feature vectors of the atoms of the second compound for each of the molecular configurations, wherein the weighted vector is determined by a machine-learning algorithm.

7. The method of claim 1, wherein determining a property of the docked second compound based on the energy scores comprises ranking the energy scores.

8. The method of claim 1, wherein the input file of the second compound includes a chemical formula of the second compound.

9. The method of claim 1, wherein the plurality of molecular descriptors associated with the second compound comprises a graphic representation of the second compound.

10. A non-transitory computer-readable storage medium storing instructions that, when executed by one or more processors, cause the processors to perform a method for predicting molecule properties, the method comprising:
   determining a plurality of molecular descriptors associated with a first compound;
   determining one or more three-dimensional (3D) conformations of the first compound;
   training a neural network using a training set comprising:
      the plurality of molecular descriptors associated with the first compound, and
      the one or more 3D conformations of the first compound, wherein training the neural network comprises determining a plurality of features that affect energies of the one or more 3D conformations of the first compound;

receiving an input file of a second compound;

implementing the neural network to determine, based on the input file and a plurality of molecular descriptors associated with the second compound, molecular configurations of the second compound docketed in a protein;

generating, using the neural network, one or more three dimensional (3D) 3D models of the second compound based on the determined molecular configurations of the second compound;

determining, using the neural network, energy scores of the one or more 3D models; and determining, using the neural network, properties of the docked compound based on the energy scores.

11. The non-transitory computer-readable storage medium of claim 10, wherein the property includes at least one of water solubility, pKa value, equilibrium dissociation constant (KD), inhibitor constant (Ki), docking pose ranking, absorption property, distribution property, metabolism property, excretion property, or toxicity of the second compound.

12. The non-transitory computer-readable storage medium of claim 10, wherein implementing the neural network to determine the molecular configurations of the second compound docketed in the protein comprises:

extracting features associated with the molecular configurations of the second compound docketed in the protein; and constructing, based on the extracted features, feature vectors associated with the molecular configurations of the second compound.

13. The non-transitory computer-readable storage medium of claim 12, wherein determining, using the neural network, the energy scores of the one or more 3D models comprises performing at least one convolution of the feature vectors associated with the molecular configurations of the second compound.

14. The non-transitory computer-readable storage medium of claim 10, wherein determining, using the neural network, the energy scores of the one or more 3D models comprises applying a scoring function to feature vectors of atoms of the second compound for each of the molecular configurations.

15. The non-transitory computer-readable storage medium of claim 14, wherein the scoring function is a weighted scoring function that applies a weighted vector to the feature vectors of the atoms of the second compound for each of the molecular configurations, wherein the weighted vector is determined by a machine-learning algorithm.

16. The non-transitory computer-readable storage medium of claim 10, wherein determining a property of the docked second compound based on the energy scores comprises ranking the energy scores.

17. The non-transitory computer-readable storage medium of claim 10, wherein the input file of the second compound includes a chemical formula of the second compound.

18. The non-transitory computer-readable storage medium of claim 10, wherein the plurality of molecular descriptors associated with the second compound comprises a graphic representation of the second compound.

19. A computer system comprising:
a memory storing instructions; and
a processor configured to execute the instructions to perform:
determining a plurality of molecular descriptors associated with a first compound;
determining one or more three-dimensional (3D) conformations of the first compound;
training a neural network using a training set comprising:
the plurality of molecular descriptors associated with the first compound, and
the one or more 3D conformations of the first compound,
wherein training the neural network comprises determining a plurality of features that affect energies of the one or more 3D conformations of the first compound;
receiving an input file of a second compound;
implementing the neural network to determine, based on the input file and a plurality of molecular descriptors associated with the second compound, molecular configurations of the second compound docketed in a protein;
generating, using the neural network, one or more 3D models of the second compound based on the determined molecular configurations of the second compound;
determining, using the neural network, energy scores of the one or more 3D models; and
determining, using the neural network, a property of the docked second compound based on the energy scores.

20. The computer system of claim 19, wherein the property includes at least one of water solubility, pKa value, equilibrium dissociation constant (KD), inhibitor constant (Ki), docking pose ranking, absorption property, distribution property, metabolism property, excretion property, or toxicity of the second compound.

* * * * *